US009925239B2

(12) United States Patent
Schneider et al.

(10) Patent No.: US 9,925,239 B2
(45) Date of Patent: *Mar. 27, 2018

(54) TREATMENT OF X-LINKED HYPOHIDROTIC ECTODERMAL DYSPLASIA WITH A FUSION EDA1 PROTEIN

(71) Applicant: EDIMER PHARMACEUTICALS, INC., Cambridge, MA (US)

(72) Inventors: Pascal Schneider, Epalinges (CH); Christine Kowalczyk-Quintas, Lausanne (CH)

(73) Assignee: EDIMER PHARMACEUTICALS, INC., Andover, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/861,292

(22) Filed: Sep. 22, 2015

(65) Prior Publication Data

US 2016/0184393 A1 Jun. 30, 2016

Related U.S. Application Data

(63) Continuation of application No. 14/117,431, filed as application No. PCT/US2012/037251 on May 10, 2012, now Pat. No. 9,175,085.

(60) Provisional application No. 61/485,677, filed on May 13, 2011.

(51) Int. Cl.
| | |
|---|---|
| A61K 38/17 | (2006.01) |
| C07K 14/47 | (2006.01) |
| C07K 14/715 | (2006.01) |
| C07K 16/28 | (2006.01) |
| A61K 9/00 | (2006.01) |
| C07K 14/705 | (2006.01) |
| A61K 39/00 | (2006.01) |
| A61K 47/68 | (2017.01) |

(52) U.S. Cl.
CPC .......... *A61K 38/179* (2013.01); *A61K 9/0019* (2013.01); *A61K 47/6811* (2017.08); *C07K 14/47* (2013.01); *C07K 14/70575* (2013.01); *C07K 14/70578* (2013.01); *C07K 14/7151* (2013.01); *C07K 16/2866* (2013.01); *A61K 2039/505* (2013.01); *C07K 2317/24* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 7,736,657 B2 | 6/2010 | Gaide et al. | |
| 8,501,177 B2 * | 8/2013 | Gaide | C07K 14/70578 424/134.1 |
| 8,664,366 B2 | 3/2014 | Hill et al. | |
| 8,895,003 B2 * | 11/2014 | Gaide | C07K 14/70578 424/134.1 |
| 2005/0152872 A1 | 7/2005 | Gaide et al. | |

FOREIGN PATENT DOCUMENTS

| | | |
|---|---|---|
| WO | 2003068977 A2 | 8/2003 |
| WO | 2010078966 A1 | 7/2010 |

OTHER PUBLICATIONS

Japanese Office Action dated Jan. 19, 2016 received in corresponding JP patent application No. 2014-510458.
Israel Office Action dated May 23, 2016 received in corresponding IL patent application No. 229015.
Zhang, et al., "Design and optimization of a linker for fusion protein construction", Progress in Natural science, 19, pp. 1197-1200, 2009.
Schneider et al., "Mutations Leading to X-linked Hypohidrotic Ectodermal Dysplasia Affect Three Major Functional Domains in the Tumor Necrosis Factor Family Member Ectodysplasin-A", J Biol. Chem, vol. 276(22), pp. 18819-18827, 2001.
Hymowitz et al., "The Cyrstal Strctures of EDA-A1 and EDA-A2: Splice Variants with Distinct Receptor Specificity", Structure, vol. 11, pp. 1513-1520, Dec. 2003.
Edimer Pharmaceuticals Presents EDI200 Update to International Gathering of Ectodermal Dysplasia Patient Foundations, http://www.drugs.com/clinical_trials/edimer-pharmaceuticals-presents-edi200-update-intern.
Mauldin, Elizabeth A., et al. "Neonatal Treatment with Recombinant Ectodysplasin Prevents Respiratory Disease in Dogs with X-Linked Ectodermal Dysplasia" AM J Med Genet A. Sep. 2009; 2045-2049.
Gaide, et al., Permanent correction of an inherited ectodermal dysplasia with recombinant EDA. Nature Medicine, vol. 9(5), pp. 614-618, May 2003 (May 2003).
Casal, et al., Significant correction of disease after postnatal administration of recombinant ectodysplasin A in canine X-linked ectodermal dysplasia. Am J Human Genetics, vol. 81, pp. 1050-1056, Nov. 2007 (Nov. 2007).
International Search Report from International Application No. PCT/US12/37251 dated Sep. 28, 2012.
Russian Office Action (and English translation) dated May 23, 2016 received in corresponding Russian patent application No. 2013155476.

(Continued)

*Primary Examiner* — Christina M Borgeest
(74) *Attorney, Agent, or Firm* — DT Ward, PC; Donna T. Ward; Lingyun Jia (57) ABSTRACT

The invention relates to methods for the temporal administration of EDA agonists, in particular EDI200, which correlate to optimal therapeutic response windows required for the formation of any EDA-dependent structures such as ectodermal appendages. Use of the methods described allow for the design of targeted therapeutic dosing and administration regimens in order to correct or alter abnormal phenotypes associated with genetic disorders, in particular, XLHED.

7 Claims, 7 Drawing Sheets

(56) References Cited

OTHER PUBLICATIONS

Extended European Search Report dated Mar. 23, 2017 received in corresponding European patent application No. 16199966.9.
Japanese Office Action (and English translation) dated Mar. 28, 2017 received in corresponding Japanese patent application No. 2016-117831.

* cited by examiner

FIG. 1A

FIG. 1B  Guard hair induction in Tabby mice with Fc-EDA

FIG. 3B Tail hair induction in Tabby mice with Fc-EDA1

FIG. 4A WT

FIG. 4B Fc-EDA P1 to P2

~4 days

FIG. 4C

| | E11.5 | E12.5 | E13.5 | E14.5 | E15.5 | E16.5 | E17.5 | E18.5 | E19.5 | E20/P1 | P2 | P3 | P4 | P5 | P6 |
|---|---|---|---|---|---|---|---|---|---|---|---|---|---|---|---|
| Dorsal | --- | nd | --- | --- | nd | + | ++ | nd | ++ | + | --- | --- | --- | | |
| Ventral | --- | nd | --- | --- | nd | --- | --- | nd | ++ | ++ | + | --- | --- | | |

FIG. 5A

FIG. 5B Eye phenotype correction in Tabby mice with Fc-EDA1

Replace genetically deficient EDA protein by a recombinant EDA (Fc-EDA) at the time when responsive cells express EDAR (in utero or shortly after birth).

FIG. 7B

Fc-EDA induces signals in EDA-deficient mice. Dose and time of administration can be controlled. in newborn; ip
in fetuses; iv in mother (transplacental transport)

FIG. 7C

EDAR-Fc serves to optionally blocks Fc-EDA signal in treated EDA-deficient mice. Use an excess of EDAR-Fc to control time of Fc-EDA signal termination.

TREATMENT OF X-LINKED HYPOHIDROTIC ECTODERMAL DYSPLASIA WITH A FUSION EDA1 PROTEIN

CROSS REFERENCE TO RELATED APPLICATIONS

This application is a Continuation of U.S. patent application Ser. No. 14/117,431 filed Jan. 22, 2014, which is a 35 U.S.C. § 371 U.S. National Stage Entry of International Application No. PCT/US2012/037251 filed May 10, 2012, which claims the benefit of priority of U.S. Provisional Patent Application Ser. No. 61/485,677 filed May 13, 2011; the contents of each of which are incorporated herein by reference in their entireties.

REFERENCE TO SEQUENCE LISTING

The present application is being filed along with a Sequence Listing in electronic format. The Sequence Listing is provided as a file entitled 2003-1000USCONSEQLST.txt, created on Sep. 15, 2015, which is 3, 710 bytes in size. The information in the electronic format of the sequence listing is incorporated herein by reference in its entirety.

FIELD OF THE INVENTION

The invention relates to compositions, methods, assays and kits for altering and/or modifying the phenotype of an individual diagnosed with or suffering from XLHED.

BACKGROUND OF THE INVENTION

X-linked hypohidrotic ectodermal dysplasia (XLHED) is a disease identified in humans, dogs, mice and cattle. A subset of the human disease has been attributed to a defect in the EDA gene (formerly ED1) that encodes for the protein ectodysplasin (EDA, subtype EDA-A1) which has been shown to be involved in the morphogenesis of hair follicles and tooth buds during early development. The disease phenotype is sparse or absent hair, missing and/or malformed teeth, hypoplastic eccrine glands, recurrent benign infections, and increased susceptibility to bronchitis and pneumonia (Reed et al., 1970; Nordgarden et al., 2001). There is significant morbidity and mortality in affected children due to hyperthermia, caused by the inability to sweat. Significant morbidities include increased risk of respiratory tract infections, ocular disease due to dry eyes, as well as difficulties with mastication, growth retardation, poor appearance, and speech impairment resulting from tooth abnormalities (delayed dentition, conical tooth crowns (peg-shaped teeth) and oligodontia).

The first model of XLHED was identified in mice selected from the Black 6 strain for large size which resulted in the spontaneous appearance of a sub-strain with abnormal hair and tooth development. The affected animals (designated "Tabby mice" due to the resemblance of the fur patterning of the heterozygote females to that of the tabby cat) lack functional EDA protein due to a frame-shift mutation resulting in the absence of the domain necessary for receptor binding and signaling that is critical for normal tooth, hair and sweat gland morphogenesis (Ferguson et al., 1997; Srivastava et al., 1997). Consequently, these mice have no sweat glands and no hair on the tail. The Tabby mouse currently is a widely used model for XLHED.

SUMMARY OF THE INVENTION

The TNF family ligand ectodysplasin A (EDA) and its receptor EDAR are required for proper development of skin appendages such as hair, teeth and eccrine sweat glands. "Loss of function" EDA mutations cause X-linked hypohidrotic ectodermal dysplasia (XLHED), a condition that can be ameliorated in mice and dogs by timely administration of recombinant EDA.

According to the present invention, methods are provided for the temporal administration of EDA agonists, in particular EDI200, which correlate to therapeutic response windows required for the formation of any EDA-dependent structures such as ectodermal appendages.

Different EDA-dependent structures can be induced at distinct time points, and may require different doses or exposure time. Interestingly, some structures can be induced up to several days after their normal development time. This property is of interest when considering EDAR agonists for therapeutic purposes.

In one embodiment, the recombinant form of EDA-A1 (herein referred to as EDI200, Fc:EDA1 or Fc-EDA) consisting of the extracellular domain of the protein fused to a portion of an immunoglobulin is used to correct phenotype abnormalities in the mammalian fetus as well as postnatally. EDI200 contains the receptor binding domain of the normally active form required for EDA signaling. As a control, EDAR-Fc, a recombinant protein consisting of the extracellular domain of the EDA receptor fused to the Fc portion of an immunoglobulin, was used as an inhibitor of EDI200 in order to control the duration of EDI200 activity in vivo.

It has now been demonstrated that there exists a time course of EDA receptor (EDAR) expression in mammals and that there are unique windows of efficacy for administration of EDI200 (Fc:EDA1) in order to correct abnormal phenotypes associated with the absence of EDA signaling such as those seen in patients with XLHED.

BRIEF DESCRIPTION OF THE FIGURES

FIG. 1 is a 3×3 panel of photographs taken of WT and Tabby mice showing that guard hairs are rescued when mice were treated in utero. FIG. 1B: Schematic representation of the results. The relevant period for EDA-dependent development of skin-derived appendages in Tabby mice is divided in 24 h periods (rectangles), with time indicated as embryonic gestation days (E11.5, E12.5, etc. . . . ) and post-natal days of life (P1, P2, etc . . . , with P1 being the day of birth). Indications in the rectangles refer to the degree to which the Tabby phenotype was reverted (---: no reversion, like Tabby. +: some reversion. ++: extensive reversion, similar to WT. nd: not determined. The curve above represents the deduced treatment opportunity window for guard hair formation in Tabby mice.

FIG. 2 is a 3×3 panel of photographs taken of WT and Tabby mice showing that sweat glands are rescued when mice were treated in utero and postnatally. FIG. 2B: Schematic representation of the results. The relevant period for EDA-dependent development of skin-derived appendages in Tabby mice is divided in 24 h periods (rectangles), with time indicated as embryonic gestation days (E11.5, E12.5, etc . . . ) and post-natal days of life (P1, P2, etc . . . , with P1 being the day of birth). Indications in the rectangles refer to the degree to which the Tabby phenotype was reverted (---: no reversion, like Tabby. +: some reversion. ++: extensive reversion, similar to WT. nd: not determined). The curve above represents the deduced treatment opportunity window for sweat gland formation in Tabby mice.

FIG. 3 is a 3×3 panel of photographs taken of WT and Tabby mice showing that tail hairs are rescued when mice were treated in utero and postnatally. FIG. 3B: Schematic representation of the results. The relevant period for EDA-dependent development of skin-derived appendages in Tabby mice is divided in 24 h periods (rectangles), with time indicated as embryonic gestation days (E11.5, E12.5, etc. . . . ) and post-natal days of life (P1, P2, etc . . . , with P1 being the day of birth). Indications in the rectangles refer to the degree to which the Tabby phenotype was reverted (---: no reversion, like Tabby. +: some reversion. ++: extensive reversion, similar to WT. nd: not determined). The curves above represent the deduced treatment opportunity windows for tail hair formation on the dorsal and ventral sides of the tail in Tabby mice, as indicated.

FIG. 4 is a panel of photographs taken of WT and Tabby mice showing that tail hairs can be induced with several days of delay.

FIG. 5 is a panel of photographs taken of WT and Tabby mice showing that the eyes are rescued when mice were treated in utero and postnatally. FIG. 5B: Schematic representation of the results. The relevant period for EDA-dependent development of skin-derived appendages in Tabby mice is divided in 24 h periods (rectangles), with time indicated as embryonic gestation days (E11.5, E12.5, etc. . . . ) and post-natal days of life (P1, P2, etc . . . , with P1 being the day of birth). Indications in the rectangles refer to the degree to which the Tabby phenotype was reverted (---: no reversion, like Tabby. +: some reversion. ++: extensive reversion, similar to WT. nd: not determined).

FIG. 6 is a panel of photographs taken of WT and Tabby mice showing that various teeth are rescued at various times when mice were treated in utero and postnatally. FIG. 6B: Schematic representation of the results. The relevant period for EDA-dependent development of skin-derived appendages in Tabby mice is divided in 24 h periods (rectangles), with time indicated as embryonic gestation days (E11.5, E12.5, etc. . . . ) and post-natal days of life (P1, P2, etc . . . , with P1 being the day of birth). Indications in the rectangles refer to the degree to which the Tabby phenotype was reverted (---: no reversion, like Tabby. +: some reversion. ++: extensive reversion, similar or bigger than WT. nd: not determined). The curves above represent the deduced treatment opportunity windows for molars formation on the lower jaw of Tabby mice. M1, M2, M3: molars 1, 2 and 3.

FIG. 7 is a diagram of the general procedure of the experiments described herein.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of methods featured in the invention, suitable methods and materials are described below.

Definitions

For convenience, the meaning of certain terms and phrases employed in the specification, examples, and appended claims are provided below. The definitions are not meant to be limiting in nature and serve to provide a clearer understanding of certain aspects of the present invention.

The term "activation" as used herein refers to any alteration of a signaling pathway or biological response including, for example, increases above basal levels, restoration to basal levels from an inhibited state, and stimulation of the pathway above basal levels.

The term "aligned development window" means the correlative timeframes between two or more species in their development of a phenotype. Aligned development windows may reflect treatment windows where the development of two species is in concordance. Aligned development windows may also provide the basis on which to define "leading", "delayed" or "expanded" treatment windows. Use of the term "aligned" herein is not meant to imply that the start and stop points of the windows match exactly. One of skill in the art appreciates that development between any two organisms (even of the same species) will not occur in exactly the same way at exactly the same time. Therefore, it is appreciated that intra- and inter-species variations do occur and that "aligned" is meant to refer to those aligned developmental windows (inclusive of the slight variations) accepted by one of skill in the art.

The term "biological sample" or "biologic sample" refers to a sample obtained from an organism (e.g., a human patient) or from components (e.g., cells) or from body fluids (e.g., blood, serum, sputum, urine, etc) of an organism. The sample may be of any biological tissue, organ, organ system or fluid. The sample may be a "clinical sample" which is a sample derived from a patient. Such samples include, but are not limited to, sputum, blood, blood cells (e.g., white cells), amniotic fluid, plasma, semen, bone marrow, and tissue or core, fine or punch needle biopsy samples, urine, peritoneal fluid, and pleural fluid, or cells therefrom. Biological samples may also include sections of tissues such as frozen sections taken for histological purposes. A biological sample may also be referred to as a "patient sample."

The term "correlate" or "correlation" as used herein refers to a relationship between two or more random variables or observed data values. A correlation may be statistical if, upon analysis by statistical means or tests, the relationship is found to satisfy the threshold of significance of the statistical test used.

A "development window" is a timeframe for which one or more phenotypes normally develop in an organism.

The term "embryo" means an unborn offspring in the process of development.

The term "embryonic stage" refers to any of the phases through which an embryo passes in development. Embryonic stages have been classified by several methods including the Carnegie stage system and the Theiler stage system.

The term "cell type" refers to a cell from a given source (e.g., a tissue, organ) or a cell in a given state of differentiation, or a cell associated with a given pathology or genetic makeup.

The term "condition" refers to the status of any cell, organ, organ system or organism. Conditions may reflect a disease state or simply the physiologic presentation or situation of an entity. Conditions may be characterized as phenotypic conditions such as the macroscopic presentation of a disease or genotypic conditions such as the underlying gene or protein expression profiles associated with the condition. Conditions may be benign or malignant.

The term "detectable" refers to an RNA expression pattern which is detectable via the standard techniques of polymerase chain reaction (PCR), reverse transcriptase-(RT) PCR, differential display, and Northern analyses, or any method which is well known to those of skill in the art. Similarly, protein expression patterns may be "detected" via standard techniques such as Western blots.

"Mammal" for purposes of treatment refers to any animal classified as a mammal, including humans, domestic and farm animals, and zoo, sports, or pet animals, such as dogs, horses, cats, cows, monkeys etc. Preferably, the mammal is a human.

The phrase "a method of treating" or its equivalent, when applied to, for example, XLHED refers to a procedure or course of action that is designed to reduce, eliminate or alter the phenotypic presentation and/or side effects associated with a disease or condition in an individual, or to alleviate the symptoms of said disease or condition. "A method of treating" a disease or disorder does not necessarily mean that the disease or disorder other disorder will, in fact, be completely eliminated, or that the symptoms of the disease or other disorder will, in fact, be completely alleviated. Often, a method of treating cancer will be performed even with a low likelihood of success, but which, given the medical history and estimated survival expectancy of an individual, is nevertheless deemed an overall beneficial course of action.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The term "prenatal" means before birth or during pregnancy.

The term "postnatal" means after birth.

The term "phenotypic presentation" refers to the macroscopic presentation of a disease.

The term "predicting" means a statement or claim that a particular event will, or is very likely to, occur in the future.

The term "prognosing" means a statement or claim that a particular biologic event will, or is very likely to, occur in the future.

The term "progression" or "disease progression" means the advancement or worsening of or toward a disease or condition.

The term "subject" refers to patients of human or other vertebrates in particular mammal and includes any individual it is desired to examine or treat using the methods according to the present invention. However, it will be understood that "patient" does not automatically imply that symptoms or diseases are present. As used herein, the term "patient" preferably refers to a human in need of treatment.

The term "treating" as used herein, unless otherwise indicated, means reversing, alleviating, inhibiting the progress of, or preventing, either partially or completely, the phenotypic manifestations of a disease or condition. The term "treatment" as used herein, unless otherwise indicated, refers to the act of treating.

The term "treatment outcome" means the result of one or more treatments. Treatment outcomes may be positive or negative. The nature of the treatment outcome, such as a "positive" outcome may be objectively or subjectively measured. For example, a positive outcome may be reflected in the subjective characterization of the patient of their condition (e.g., the "feel" better), or it may be represented by an objective measurement of the disorder (e.g., an increase in hair growth, tooth morphology or ability to sweat).

The term "treatment window" as used herein refers to the timeframe within which administration of a pharmaceutical composition will exert at least some positive treatment outcome. Treatment windows may be measured in hours, days, weeks, months or years. They may also occur at a time just after fertilization but prior to embryo implantation, when the organism is in utero or at any time prior to birth, or after. To this end, it follows that a treatment window for an organism from conception to birth (including in utero) may be characterized in terms of treatment of the mother. In this instance, contacting the mother with the pharmaceutical composition is analogous to "treatment" of the embryo or fetus even though referred to as treatment of the mother. Treatment windows may coincide with "aligned development windows." Treatment windows may be leading, delayed or expanded.

The term "expanded treatment window" means a timeframe during which treatment may be administered that is longer in duration than a treatment window based solely on an aligned development window. Expanded treatment windows may begin or end coincident with the beginning or ending of an aligned development window and extend either earlier or later in time. They may also be longer than an aligned development window and extend both earlier and later in time, thereby being inclusive of one or more aligned development windows. Expanded treatment windows may be expressed in terms of hours, days, weeks, months or years. Expanded treatment windows may be 1-20%, 2-30%, 5-50% or more longer than the normal development window constituting the aligned development window. They may be 3×, 4×, 5× or more longer.

The term "delayed treatment window" means a timeframe during which treatment may be administered that begins later in time later than a treatment window based solely on an aligned development window. Delayed treatment windows begin at some time point after an expected aligned development window and extend later in time. They may extend indefinitely and may cover one or more subsequent aligned development windows. Delayed treatment windows may be expressed in terms of hours, days, weeks, months or years. Delayed treatment windows may be 1-20%, 2-30%, 5-50% or more longer than the normal development window constituting the aligned development window. They may be 3×, 4×, 5× or more longer. If they are longer than an aligned development window, then by definition the delayed treatment window is an expanded treatment window that simply starts at a later time.

The term "leading treatment window" means a timeframe during which treatment may be administered that begins earlier in time than a treatment window based solely on an aligned development window. Leading treatment windows begin prior to the beginning of an expected aligned development window. They may also be longer than an aligned development window and extend into and beyond one or more aligned development windows. Leading treatment windows may be expressed in terms of hours, days, weeks, months or years. Leading treatment windows may be 1-20%, 2-30%, 5-50% or more longer than the normal development window constituting the aligned development window. They may be 3×, 4×, 5× or more longer. If they are longer than an aligned development window, then by definition the leading treatment window is an expanded treatment window that simply starts at an earlier time.

The term "therapeutically effective agent" means a composition that will elicit the biological or medical response of a tissue, organ, system, organism, animal or human that is being sought by the researcher, veterinarian, medical doctor or other clinician.

The term "therapeutically effective amount" or "effective amount" means the amount of the subject compound or combination that will elicit the biological or medical response of a tissue, organ, system, organism, animal or human that is being sought by the researcher, veterinarian, medical doctor or other clinician. In this context, a biological or medical response includes treatment outcomes.

Alteration or Modification of Phenotypic Presentation

The present invention provides methods for the correction, alteration or mitigation of various phenotypic presentations associated with ectodermal dysplasia, specifically XLHED. Phenotypic presentations of ectodermal dysplasia include, but are not limited to, missing or abnormally shaped teeth (including, but not limited to, any of the first, second or third molars, or the first or second premolar, canine or first or second incisors), abnormal morphology or lack of sweat glands, Meibomian glands, glands of the upper respiratory tract, sebaceous glands, salivary glands and other glands, lack or abnormal morphology of various types of hair, and alopecia.

Correction, alteration and/or mitigation of the phenotypic presentations associated with XLHED are accomplished by the administration of a recombinant form of the ligand for the EDA receptor. Such recombinant EDA compositions include those described in detail in U.S. patent application Ser. No. 12/756,268 filed Apr. 8, 2010 which is a continuation of U.S. patent application Ser. No. 10/503,999 filed Oct. 25, 2004, now granted U.S. Pat. No. 7,736,657, which is a 35 U.S.C. Section 371 National Phase Entry Application of International Application No. PCT/EP2002/009354 filed Aug. 21, 2002, which designates the U.S., and which claims the benefit of priority of German Application No. 10205368.5 filed Feb. 10, 2002 and German Application No.

10205583.1 filed Feb. 11, 2002, the contents of which are incorporated herein by reference in their entireties.

In one embodiment of the invention, the recombinant fusion protein is EDI200 (a.k.a., Fc-EDA, Fc:EDA1). EDI200 is a fully humanized Fc fusion protein consisting of the Fc region of human IgG1 and the receptor binding domain (Tumor Necrosis Factor (TNF) domain) of EDA-A1. The biologically active protein is glycosylated and exists primarily as a hexamer, comprised of six identical Fc:EDA-A1 monomeric species. The 380 amino acid sequence of the monomeric species is provided herein as SEQ ID NO: 1.

Administration and Dosing

When the organism to be treated is a mammal such as a human, the composition may be administered by any means known in the art including, but not limited to oral, intraperitoneal, or parenteral routes, including intracranial (e.g., intraventricular, intraparenchymal and intrathecal), intravenous, intramuscular, subcutaneous, transdermal, airway (aerosol), nasal, rectal, and topical (including buccal and sublingual) administration. In certain embodiments, the compositions are administered by intravenous infusion or injection.

In general, a suitable dose of EDI200 will be in the range of 0.01 to 200.0 milligrams per kilogram body weight of the recipient, patient or individual per day, generally in the range of 1 to 50 mg per kilogram body weight per day. For example, EDI200 can be administered at 0.05 mg/kg, 0.5 mg/kg, 1 mg/kg, 1.5 mg/kg, 2 mg/kg, 3 mg/kg, 3.5 mg/kg, 7 mg/kg, 10 mg/kg, 20 mg/kg, 30 mg/kg, 40 mg/kg, or 50 mg/kg per single dose. The pharmaceutical composition may be administered once daily, or may be administered as two, three, or more sub-doses at appropriate intervals throughout the day or even using continuous infusion or delivery through a controlled release formulation. In that case, EDI200 contained in each sub-dose must be correspondingly smaller in order to achieve the total daily dosage. Dosing may also be according to multi-dosing schemes of one, two, three or more doses. The dosage unit can also be compounded for delivery over several days, e.g., using a conventional sustained release formulation which provides sustained release over a several day period. Sustained release formulations are well known in the art and are particularly useful for delivery of agents at a particular site, such as could be used with the agents of the present invention. In this embodiment, the dosage unit contains a corresponding multiple of the daily dose.

The effect of a single dose on any particular phenotype or symptom can be long lasting, such that subsequent doses are administered at not more than 3, 4, or 5 day intervals, or at not more than 1, 2, 3, or 4 week intervals.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual pharmaceutical compositions encompassed by the invention can be made using conventional methodologies or on the basis of in vivo testing using an appropriate animal model.

The present invention also includes pharmaceutical compositions and formulations that include the EDI200 compounds featured in the invention. The present invention also contemplates the use of combinations of compounds or combinations of treatment regimens, each of which have as a component administration of a pharmaceutical composition comprising EDI200. The pharmaceutical compositions of the present invention may be administered in a number of ways depending upon whether local or systemic treatment is desired and upon the area to be treated. Administration may be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration. EDI200 can be delivered in a manner to target a particular tissue.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Suitable topical formulations include those in which EDI200 is in an admixture with a topical delivery agent such as lipids, liposomes, fatty acids, fatty acid esters, steroids, chelating agents and surfactants.

In one embodiment of the invention, the subject, patient or individual receiving treatment with a pharmaceutical composition comprising EDI200 is the mother of the individual expressing the abnormal phenotype. In this instance, she may be treated at any time post-conception (fertilization).

In one embodiment, the mother is treated within 3 days of fertilization. In another embodiment, the mother is treated prior to implantation of the embryo. In one embodiment the mother is treated after implantation of the embryo. The mother may be treated at any time during gestation of the embryo, or postnatally. If treated during gestation, treatment may be continuous over a number of hours, days or weeks. Treatment may be discontinuous or intermittent. If treated during gestation of her embryo, treatment may be during one or more specified Carnegie stages of her embryo, either sequential or separated, in time. In one embodiment, the mother is treated at time when her offspring may receive an effective amount of EDI200 from the mother when she is lactating. In this embodiment, the mother may be treated at any time prior to (or after) the birth of the offspring wherein EDI200 may be found in the lactation fluids (e.g., breast milk) of the mother.

In one embodiment, the mother is contacted with a pharmaceutical composition comprising EDI200 at one or more times within Carnegie stages 17-23. In one embodiment, the mother is treated between Carnegie stage 17 and 22. In one embodiment, the mother is treated during one of Carnegie stages, 17, 18, 19, 20, 21, 22 or 23. Treatment may also span one or more stages in whole or in part.

Determination of the treatment window for humans may be accomplished via correlative data from one or more representative animal models where developmental stages have been aligned. Such alignments accepted in the art are those of the Carnegie and Thieler stages. Furthermore and according to the present invention, the range of such aligned treatment widows may vary. Variations may be based on other evidence of developmental process differences known in the art. For example, should a phenotype have been shown to be rescued outside of an aligned development window, the treatment window may be adjusted to account for these data.

In one example, it is known that tail hair initiation in the mouse can still take place 4 days after normal development when animals were treated with EDI200. In such a case, the treatment window would coincide with a later Carnegie or Theiler stage and hence be a delayed or enlarged treatment window. Therefore, it should be understood that according to the present invention, treatment windows may be augmented by differences in development such that treatment may be necessary prior to the normal development process of the phenotype in question, after the normal development process of the phenotype in question or along a dosing schedule that is expanded to embrace more than a single development window or aligned development window.

Determination of the treatment window available to the mother which will alter or modify an abnormal phenotype in the birthed offspring can be made by measuring markers in the pregnant mothers blood or serum which provide correlations to the age of the embryo. Such measurements include, but are not limited to, human chorionic gonadotropin (hCG), hormones such as estrogen, testosterone, progesterone, other bio-indicators of the mother or fetus' status including glucose, proteins and the like. Physical measurements of the embryo or fetus may also inform the appropriate treatment windows. These measurements have the advantage of being non-invasive yet precise. Once such method includes fetal measurements obtained via ultrasound.

It remains the case that should the embryo or fetus require treatment with the compositions of the present invention, such as EDI200, methods are available to deliver the compositions directly to the embryo via endoscopic, surgical or micro-surgical techniques. Delivery by such methods may be to a cell, tissue, organ or organ system of the fetus or to the amniotic fluid surrounding the fetus.

The present invention also provides for the treatment of the offspring after birth. Depending on the phenotype to be altered, certain treatment windows remain open after birth. Treatment of the offspring can be at any time after birth but preferably in the first year of life.

In one embodiment, where tooth morphology presents as abnormal, later treatment with pharmaceutical compositions comprising EDI200 is possible.

Human Embryo Stages

Across the first 60 days of human gestation, 23 distinct morphological "Carnegie" stages (so named because the work was begun at the Carnegie Institution) have been identified based on averages of such features as number of somites, and embryonic length. An embryo is assigned a Carnegie stage (numbered from 1 to 23) based on its external features. Stages are based on the external and/or internal morphological development of the vertebrate embryo, and are not directly dependent on either age or size. The human embryonic period proper is divided into 23 Carnegie stages. These are summarized in Table 1.

TABLE 1

Carnegie Stages of Human Embryo Development

| Stage | Days | Size (mm) | Events |
|---|---|---|---|
| 1 | 1 | 0.1-0.15 | fertilized oocyte, pronuclei |
| 2 | 2-3 | 0.1-0.2 | cell division with reduction in cytoplasmic volume, formation of inner and outer cell mass |
| 3 | 4-5 | 0.1-0.2 | loss of zona pellucida, free blastocyst |
| 4 | 5-6 | 0.1-0.2 | attaching blastocyst |
| 5 | 7-12 | 0.1-0.2 | implantation |

TABLE 1-continued

Carnegie Stages of Human Embryo Development

| Stage | Days | Size (mm) | Events |
|---|---|---|---|
| 6 | 13-15 | 0.2 | extraembryonic mesoderm, primitive streak |
| 7 | 15-17 | 0.4 | gastrulation, notochordal process |
| 8 | 17-19 | 1.0-1.5 | primitive pit, notochordal canal |
| 9 | 19-21 | 1.5-2.5 | Somite Number 1-3 neural folds, cardiac primordium, head fold |
| 10 | 22-23 | 2-3.5 | Somite Number 4-12 neural fold fuses |
| 11 | 23-26 | 2.5-4.5 | Somite Number 13-20 rostral neuropore closes |
| 12 | 26-30 | 3-5 | Somite Number 21-29 caudal neuropore closes |
| 13 | 28-32 | 4-6 | Somite Number 30 leg buds, lens placode, pharyngeal arches |
| 14 | 31-35 | 5-7 | lens pit, optic cup |
| 15 | 35-38 | 7-9 | lens vesicle, nasal pit, hand plate |
| 16 | 37-42 | 8-11 | nasal pits moved ventrally, auricular hillocks, foot plate |
| 17 | 42-44 | 11-14 | finger rays |
| 18 | 44-48 | 13-17 | ossification commences |
| 19 | 48-51 | 16-18 | straightening of trunk |
| 20 | 51-53 | 18-22 | upper limbs longer and bent at elbow |
| 21 | 53-54 | 22-24 | hands and feet turned inward |
| 22 | 54-56 | 23-28 | eyelids, external ears |
| 23 | 56-60 | 27-31 | rounded head, body and limbs |

Mouse Embryo Stages

Mouse embryos can be staged according to a variety of criteria, the most general of which are those described by Theiler in "The House Mouse: Atlas of Mouse Development" (Springer-Verlag, New York, 1989). The data in Table 2 refer to embryos of crosses between F1 hybrid (C57BL X CBA) mice. The table was excerpted from the EMAP eMouse Atlas Project which can be accessed through www.emouseatlas.org. The column "dpc" represents days post conception, with the morning after the vaginal plug is found being designated 0.5 dpc (or E0.5).

TABLE 2

Theiler Stages of Mouse Embryo Development

| Theiler Stage | dpc | (C57BLxCBA) F1 mice |
|---|---|---|
| 1 | 0-0.9 | One-cell egg |
| 2 | 1 | Dividing egg |
| 3 | 2 | Morula |
| 4 | 3 | Blastocyst, Inner cell mass apparent |
| 5 | 4 | Blastocyst (zona-free) |
| 6 | 4.5 | Attachment of blastocyst, primary endoderm covers blastocoelic surface of inner cell mass |
| 7 | 5 | Implantation and formation of egg cylinder Ectoplacental cone appears, enlarged epiblast, primary endoderm lines mural trophectoderm |
| 8 | 6 | Differentiation of egg cylinder. Implantation sites 2 × 3 mm. Ectoplacental cone region invaded by maternal blood, Reichert's membrane and proamniotic cavity form |
| 9a | 6.5 | Pre-streak (PS), advanced endometrial reaction, ectoplacental cone invaded by blood, extraembryonic ectoderm, embryonic axis visible, |
| 9b | | Early streak (ES), gastrulation starts, first evidence of mesoderm |
| 10a | 7 | Mid streak (MS), amniotic fold starts to form |
| 10b | | Late streak, no bud (LSOB), exocoelom |
| 10c | | Late streak, early bud (LSEB), allantoic bud first appears, node, amnion closing |
| 11a | 7.5 | Neural plate (NP), head process developing, amnion complete |
| 11b | | Late neural plate (LNP), elongated allantoic bud |
| 11c | | Early head fold (EHF) |
| 11d | | Late head fold (LHF), foregut invagination |

TABLE 2-continued

Theiler Stages of Mouse Embryo Development

| Theiler Stage | dpc | (C57BLxCBA) F1 mice |
|---|---|---|
| 12a | 8 | 1-4 somites, allantois extends, 1st branchial arch, heart starts to form, foregut pocket visible, preotic sulcus at 2-3 somite stage) |
| 12b | | 5-7 somites, allantois contacts chorion at the end of TS12 Absent 2nd arch, >7 somites |
| 13 | 8.5 | Turning of the embryo, 1st branchial arch has maxillary and mandibular components, 2nd arch present Absent 3rd branchial arch |
| 14 | 9 | Formation & closure of ant. neuropore, otic pit indented but not closed, 3rd branchial arch visible Absent forelimb bud |
| 15 | 9.5 | Formation of post. neuropore, forelimb bud, forebrain vesicle subdivides Absent hindlimb bud, Rathke's pouch |
| 16 | 10 | Posterior neuropore closes, Formation of hindlimb & tail buds, lens plate, Rathke's pouch; the indented nasal processes start to form Absent thin & long tail |
| 17 | 10.5 | Deep lens indentation, adv. devel. of brain tube, tail elongates and thins, umbilical hernia starts to form Absent nasal pits |
| 18 | 11 | Closure of lens vesicle, nasal pits, cervical somites no longer visible Absent auditory hillocks, anterior footplate |
| 19 | 11.5 | Lens vesicle completely separated from the surface epithelium. Anterior, but no posterior, footplate. Auditory hillocks first visible Absent retinal pigmentation and sign of fingers |
| 20 | 12 | Earliest sign of fingers (splayed-out), posterior footplate apparent, retina pigmentation apparent, tongue well-defined, brain vesicles clear Absent 5 rows of whiskers, indented anterior footplate |
| 21 | 13 | Anterior footplate indented, elbow and wrist identifiable, 5 rows of whiskers, umbilical hernia now clearly apparent Absent hair follicles, fingers separate distally |
| 22 | 14 | Fingers separate distally, only indentations between digits of the posterior footplate, long bones of limbs present, hair follicles in pectoral, pelvic and trunk regions Absent open eyelids, hair follicles in cephalic region |
| 23 | 15 | Fingers & Toes separate, hair follicles also in cephalic region but not at periphery of vibrissae, eyelids open Absent nail primordia, fingers 2-5 parallel |
| 24 | 16 | Reposition of umbilical hernia, eyelids closing, fingers 2-5 are parallel, nail primordia visible on toes Absent wrinkled skin, fingers & toes joined together |
| 25 | 17 | Skin is wrinkled, eyelids are closed, umbilical hernia is gone Absent ear extending over auditory meatus, long whiskers |
| 26 | 18 | Long whiskers, eyes barely visible through closed eyelids, ear covers auditory meatus |
| 27 | 19 | Newborn Mouse |
| 28 | | Postnatal development |
| Adult | | Adult Mouse |

Comparisons of Embryo Stages

At birth, the mouse contains the same differentiated cell types and tissues as a human even though the mouse pup is fully developed and born only 19 days following fertilization of the egg, compared to approximately 266 days for the human. For the initial 100 hours or so of post-fertilization development, however, the mouse and human embryos are virtually indistinguishable visually from one another. These similarities have been documented many times with correlations and comparisons being updated over the years.

Consequently, it is well established to one of skill that certain windows of development, or aligned development windows, between rodent (mouse and rat) and humans exist and that these windows provide an excellent correlation of developmental timing across species. As such, treatment windows identified in non-human species may be converted into a treatment window for human species. This is not dissimilar to the reliance placed on animal models in the prediction of efficacy in humans. Table 3 provides a comparison among Human, Mouse and Rat but other species have been examined and stages calculated.

TABLE 3

Multi-species Carnegie Stages (9-15)

| Species | | 9 | 10 | 11 | 12 | 13 | 14 | 15 |
|---|---|---|---|---|---|---|---|---|
| Human | Days | 20 | 22 | 24 | 28 | 30 | 33 | 36 |
| Mouse | Days | 9 | 9.5 | 10 | 10.5 | 11 | 11.5 | 12 |
| Rat | Days | 10.5 | 11 | 11.5 | 12 | 12.5 | 13 | 13.5 |

TABLE 3b

Multi-species Carnegie Stages (16-23)

| Species | | 16 | 17 | 18 | 19 | 20 | 21 | 22 | 23 |
|---|---|---|---|---|---|---|---|---|---|
| Human | Days | 40 | 42 | 44 | 48 | 52 | 54 | 55 | 58 |
| Mouse | Days | 12.5 | 13 | 13.5 | 14 | 14.5 | 15 | 15.5 | 16 |
| Rat | Days | 14 | 14.5 | 15 | 15.5 | 16 | 16.5 | 17 | 17.5 |

Other means of identifying treatment windows for human subjects includes the use of direct and/or indirect markers of development. In one embodiment of the invention, markers of gestational age can be used to determine the administration timing of EDI200. For example, after implantation, cells within the developing placenta (syncitiotrophoblasts) synthesize and secrete Human chorionic gonadotropin (hCG) into the maternal bloodstream. The main function of serum hCG is to maintain the corpus *luteum* in the maternal ovary and therefore maintain the early pregnancy. However, as can be seen from Table 4, hCG levels in the mother's serum provides an indication as to the gestational age range of the embryo or fetus. The table was adapted from the website of Dr. Mark Hill at the University of New South Wales (UNSW).

TABLE 4

Levels of hCG in serum

| Weeks after Last Menstrual period (LMP) | Days after Fertilization | hCG level (mIU/ml or IU/L) |
|---|---|---|
| Week 3 | 7 | 0 to 5 |
| Week 4 | 14 (next period due) | 5 to 426 |
| Week 5 | 21 | 18 to 7340 |
| Week 6 | 28 | 1,080 to 56,500 |
| Weeks 7 to 8 | 35 to 42 | 7,650 to 229,000 |
| Weeks 9 to 12 | 49 to 70 | 25,700 to 288,000 |
| Weeks 13 to 16 | 77 to 100 | 13,300 to 254,000 |
| Weeks 17 to 24 | | 4,060 to 165,400 |
| Weeks 25 to birth | | 3,640 to 117,000 |

From the table it is evident that measurements of hCG can inform a clinician as to the developmental stage of the embryo and hence the timing of administration of EDI200 can be determined to provide the optimal outcome for alteration of the phenotype.

Other means of determining the most appropriate therapeutic window of administration include methods such as those reviewed and described by O'Rahilly (O'Rahilly R, et al, Developmental Stages in Human Embryos: Revised and New Measurements. Cells Tissues Organs 2010; 192:73-84), the contents of which are incorporated herein in their entirety. In these methods, the greatest length or GL (GL; defined as the length of an embryo or a fetus exclusive of the lower limbs) was measured via ultrasound and correlated with days of gestation or Carnegie stage. Table 5 summarizes the findings of O'Rahilly. Therefore, in addition to Theiler and Carnegie charts, actual measurements may be made via ultrasound of the embryo or fetus and administration of EDI200 made at a time when it would afford the greatest therapeutic efficacy as taught by the present invention.

TABLE 5

Use of Greatest Length as Treatment Window Guide

| Stage | Greatest length range (mm) | Proposed Age (days) |
|---|---|---|
| 12 | 3.9-4.9 | 29-31 |
| 13 | 4.8-5.3 | 30-33 |
| 14 | 6.7-7.8 | 33-35 |
| 15 | 8.0-8.5 | 35-37 |
| 16 | 7.0-10.9 | 37-40 |
| 17 | 11.2-13.2 | 39-42 |
| 18 | 14.0-15.5 | 42-45 |
| 19 | 16.3-18.5 | 45-47 |
| 20 | 18.5-20.8 | 47-50 |
| 21 | 22.0-22.7 | 49-52 |
| 22 | 24.0-25.8 | 52-55 |
| 23 | 27.0-32.0 | 53-58 |

Treatment or development windows may also be defined as "during gestation", at a time related to maturity at birth, a time relative to time of independence, a time of appearance or completion of primary dentition or at permanent dentition. The comparative times are listed for mouse, dog and human in Table 6.

TABLE 6

Additional Treatment Windows

| Species | Gestation | Relative Maturity at Birth | Time to Independence | Primary Dentition | Permanent Dentition |
|---|---|---|---|---|---|
| Mouse | 20 d | 27 wks | 3 wks | None | 4 wks |
| Dog | 60 d | 36 wks | 6 wks | 12 wks | 28 wks |
| Human | 265 d | 40 wks | 18 yrs | 3 yrs | 12.5 yrs |

The invention is further illustrated by the following non-limiting examples.

EXAMPLES

Example 1. Mapping Tissue Responsiveness to Recombinant EDA (Fc:EDA1)

The TNF family ligand ectodysplasin A (EDA) and its receptor EDAR are required for proper development of skin appendages such as hair, teeth and eccrine sweat glands. "Loss of function" EDA mutations cause X-linked hypohidrotic ectodermal dysplasia (XLHED), a condition that can be ameliorated in mice and dogs by timely administration of recombinant EDA or EDI200.

In an effort to determine the temporal responsiveness of tissues to EDI200 as well as the dose required and duration of EDI200 signaling necessary for the formation of any EDA-dependent structures such as ectodermal appendages, the following experiments were conducted.

Briefly, the method consists to administer an EDA-deficient animal (e.g., the Tabby mouse strain) with a biologically active Fc-EDA fusion protein, EDI200, at a chosen dose (e.g. 1 mg/kg) and at a particular time point in development, followed, after a certain time interval (e.g. 24 h), by an excess of an EDA inhibitor (e.g. the fusion protein EDAR-Fc at 30 mg/kg). The method was applicable both in utero and postnatally. Thus, the method provides for control of the timing of administration, exposure duration and dose of EDAR agonist (EDI200) in EDA-deficient mice. The results of the studies were striking. It was determined that different EDA-dependent structures can be induced at distinct time points, and may require different doses or exposure times. Interestingly, some structures can be induced up to several days after their normal development time. This finding is of great interest when considering EDAR agonists and efficacy windows for therapeutic purposes.

Study Animals

Tabby mice and their wild type counterparts were used in the in vivo assessment of EDI200. The Tabby mouse strain was white-bellied agouti B6CBAa $A^{w-J}$/A-$Eda^{Ta}$/J (000314; Jackson Laboratory) bred as $Eda^{Ta}$/$Eda^{Ta}$ and $Eda^{Ta}$/Y mutants. The WT mouse strain was in the same genetic background bred as +/+ and +/Y controls.

The Tabby phenotype in mice was the result of Ectodysplasin-A1 deficiency (Srivastava et al. 1997). This mouse strain was the animal model of XLHED and was used for gene expression and EDI200 efficacy studies. WT strain mice were the control animals for the Tabby strain mice. Male and female animals were randomly assigned to test groups. Mice were handled according to institutional and Swiss Federal Veterinary Office guidelines, with the authorization of the "office vétérinaire cantonal du canton de Vaud."

In Utero Treatment

Tabby females and males were mated overnight, then separated. Mice were weighed daily to monitor weight gain. Pregnant mice were injected intravenously (i.v.) with Fc-EDA1 (EDI200; in 150 µl PBS) at 1 mg/kg (e.g. 25 µg for a 25 g female). Twenty four hours (24) later females were injected i.v. with hEDAR-Fc at 25 to 30 mg/kg (e.g. 750 of EDAR-Fc at 4.3 mg/ml in 200 µl for a 25 g female).

Birth dates were recorded and thereafter daily photographs were taken of the tail and eye. At weaning (day 21 postbirth), photographs were taken of the tail, of the tip of tail, of guard hair, of the retro-auricular region, and of the eye. A sweat test as described in PCT Publication WO 2010/113117 and its priority document the contents of each of which are incorporated herein by reference in their entirety was also performed. At day 30 postbirth, animals were sacrificed and histology of the trachea (Alcian blue staining and hematoxinlin/eosin (H&E) stainings), of the eyelids (H&E) and of the footpads (H&E) was performed. Skulls were collected and prepared and photographs were taken of the upper and lower molars.

Postnatal Treatment

At birth pups were labeled by puncture of a footpad with a 30-gauge needle dipped in china ink. Fc-EDA at 1 mg/kg was injected intraperitoneally in 15 µl PBS on the day of birth (P1) or at P2, P3, P4 or P5. hEDAR-Fc was administrated via the same route 24 h later. The analysis of mice was performed as described above for in utero treatments.

Assessment of Phenotype Correction

The animals were visually assessed (live animals or isolated skulls or tissue sections) for correction of the Tabby phenotype concerning presence of sweat glands, molars, tracheal glands, Meibomian glands, tail hair, hair behind ears, tail kink, and eye appearance.

Sweat Test

Hind paws were painted with a solution of 3% (w/v) iodine in ethanol. Once dry, the paws were painted with a suspension of 40% (w/v) of starch in mineral oil. Photos were taken one to two minutes later. The starch iodine test was determined to be positive when black dots were visible, indicative of the presence of liquid medium and consistent with the presence of sweat glands.

Overview of Findings

Twenty four (24)-hour exposure to EDI200 in the days prior to birth or in the 7 days following birth indicated that different EDA-dependent developmental processes have different treatment opportunity windows. While some processes require short exposure to EDI200 in order for restoration of WT phenotype, others seem to require longer exposure. This may be due to multi-stage developmental processes which are in play. It was also determined that a 24 h treatment, performed at any one time during development, can only rescue a limited set of EDA-dependent phenotypes suggesting that multiple administrations may also be useful and provide broader application over multiple phenotypes. Consequently, multiple EDI200 treatments distributed throughout the developmental phase when EDA1 is active would be expected to achieve maximal restoration of the WT phenotype.

Regarding dosage, in mice it was determined that EDI200 at 1 mg/kg remains active for more than 24 hours. It was also found previously that >3.5 hours exposure of newborn Tabby mice to 2 µg EDI200 administered intravenously is sufficient to correct growth of hair on the tail (Swee et al 2009). Considering that the elimination half-life of EDI200 (45 hours) is estimated to be at least 10 times longer than the exposure period needed to obtain a biological effect, the elimination half-life of EDI200 is not a limiting factor in regards to therapeutic activity/efficacy, at least when tail hair induction is considered.

Example 2. Correction of Pre- and Post-Natal Phenotype

In order to assess a wide time frame for the ability of EDI200 to correct aspects of the Tabby phenotype by exposure of prenatal mice to EDI200, pregnant Tabby mice were intravenously administered an effective dose of EDI200 at a chosen embryonic day of development. Twenty four (24) hours later mice were intravenously administered an excess of EDAR-Fc to interrupt/neutralize the remaining circulating EDI200.

Figure 7A:
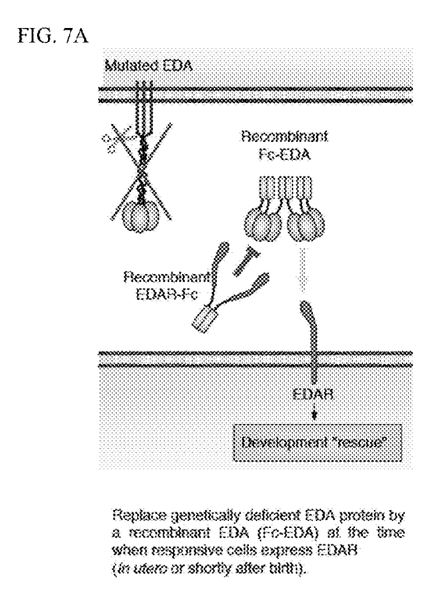
FIG. 7A: In EDA-deficient organisms (in this case mice), endogenous EDA is either not made or inactive, but the EDA receptor remains expressed in signaling-competent form. Providing recombinant EDA in the form of Fc-EDA is sufficient to activate the EDAR signaling pathway and to rescue some or all of the EDA-deficient phenotype. Treatment is effective if applied at times when endogenous EDAR can respond.
Figure 7B:
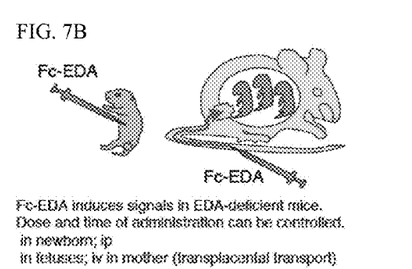
FIG. 7B: Administration of Fc-EDA can be done directly in newborn EDA-deficient mice, or indirectly in fetuses by administrating the pregnant mother with Fc-EDA. The Fc-portion allows transplacental transfer and thus access to fetuses. The dose and time of Fc-EDA administration can be chosen.
Figure 7C:
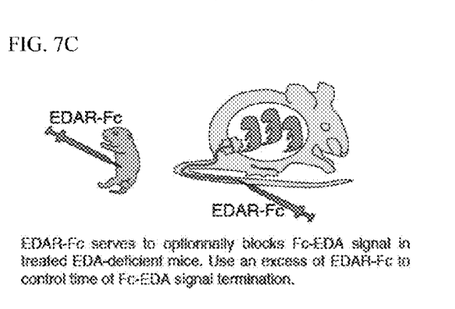
FIG. 7C: Fc-EDA action in treated EDA-deficient animals can be blocked after the desired time interval by administration of an excess of EDAR-Fc. EDAR-Fc can also reach fetal circulation by transplacental transport system.

To assess the ability of EDI200 to correct aspects of the Tabby phenotype by exposure of neonate mice to EDI200, Tabby pups were administered an effective dose of EDI200 by the intra-peritoneal route at various days post-birth. Twenty four (24) hours later mice were administered an excess of EDAR-Fc by the intra-peritoneal route to interrupt/neutralize the remaining circulating EDI200. See FIG. 7 for the general approach.

The study design was as follows: Pregnant Tabby mice were treated iv at the indicated embryonic day (E11.5 or E13.5 or E14.5 or E16.5 or E17.5) with EDI200 at 1 mg/kg, followed 24 h later by EDAR-Fc at 30 mg/kg. Alternatively, new born Tabby pups were injected ip with EDI200 at 1 mg/kg (at P1, P2, P3, P4 or P5), followed 24 h later by EDAR-Fc at 30 mg/kg. In some cases, EDI200 was administered, but EDAR-Fc was omitted (e.g. at E14.5 or at P1). When indicated, EDI200 was administered repeatedly at different time points (E18.5 and P3), and EDAR-Fc was omitted. In a negative control group, on embryonic day E13.5 pregnant Tabby mice were intravenously administered both 1 mg/kg EDI200 and 30 mg/kg EDAR-Fc. Untreated WT mice were included as controls. Development of tail hair was monitored daily for three weeks and a general assessment of correction of the Tabby phenotype was performed around postnatal day P23 for external assessment of the phenotype, and at around P30 for assessment of tooth morphology and analysis tissue sections. Three pups per liter were analyzed to assess the effect of prenatal exposure to EDI200, and three animals per group were analyzed to assess the effects of postnatal exposure to EDI200. The animals were visually assessed (live animals or tissue sections or isolated skulls) for correction of the Tabby phenotype concerning presence of sweat glands, molars, tracheal glands, Meibomian glands, tail hair, hair behind ears, tail kink, and eye appearance.

Figure 1A:
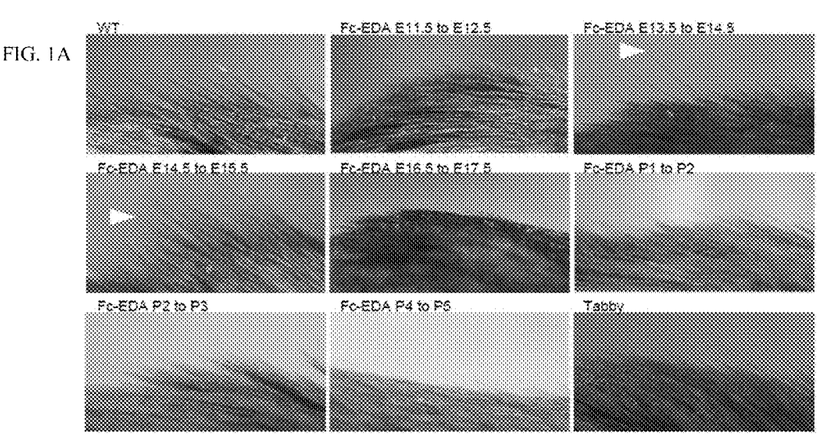
FIG. 1A: Pregnant EDA-deficient Tabby mice at days E11.5, E13.5, E14.5, E16.5, E17.5 of gestation or newborn Tabby pups at P1 (day of birth), P2, P3, P4 or P5 were administered EDI200 at 1 mg/kg iv (in mothers) or ip (in newborn), followed 24 h later by EDAR-Fc at 30 mg/kg to block remaining EDI200. Pups of treated mothers, or treated pups were analyzed at weaning for the presence of guard hair (arrowheads). Untreated WT and Tabby controls are shown for comparison. Timing of treatment is indicated on top of the pictures. The most relevant timings of treatment relative to guard hair induction are shown.
Figure 1B:
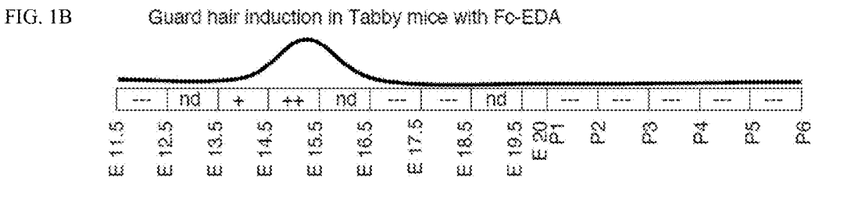
Figure 2A:
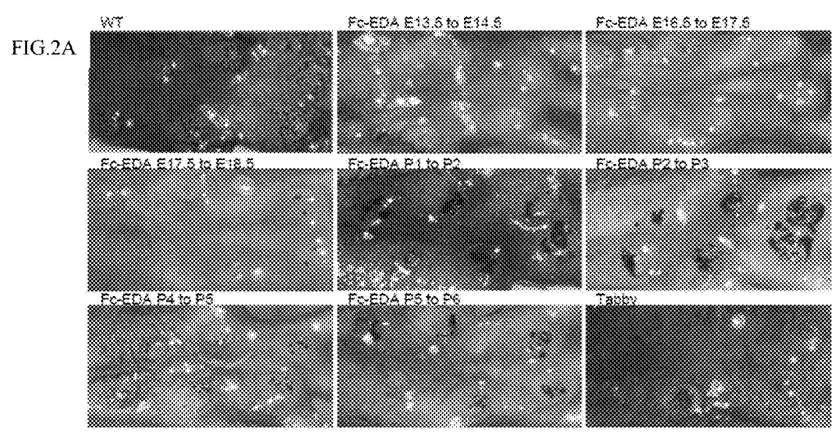
FIG. 2A: Pregnant EDA-deficient Tabby mice at days E11.5, E13.5, E14.5, E16.5, E17.5 of gestation or newborn Tabby pups at P1 (day of birth), P2, P3, P4 or P5 were administered EDI200 at 1 mg/kg iv (in mothers) or ip (in newborn), followed 24 h later by EDAR-Fc at 30 mg/kg to block remaining EDI200. Pups of treated mothers, or treated pups were analyzed at weaning for the presence of sweat glands using an iodine/starch sweat test. Sweat glands openings are visualized as black spots. Untreated WT and Tabby controls are shown for comparison. Timing of treatment is indicated on top of the pictures. The most relevant timings of treatment relative to sweat gland induction are shown.
Figure 2B:
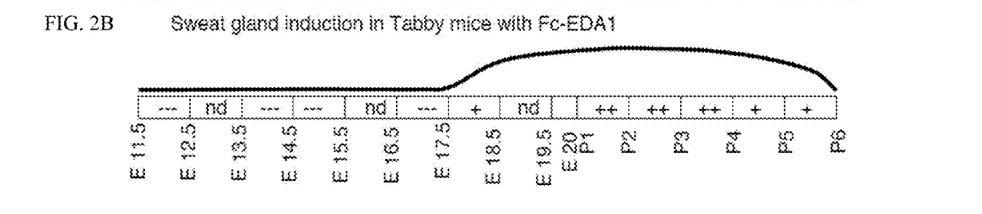
Figure 3A:
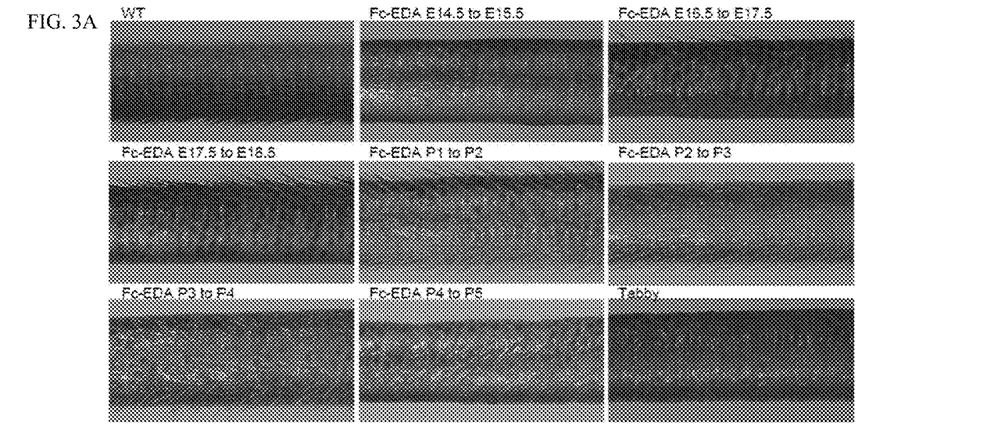
FIG. 3A: Pregnant EDA-deficient Tabby mice at days E11.5, E13.5, E14.5, E16.5, E17.5 of gestation or newborn Tabby pups at P1 (day of birth), P2, P3, P4 or P5 were administered EDI200 at 1 mg/kg iv (in mothers) or ip (in newborn), followed 24 h later by EDAR-Fc at 30 mg/kg to block remaining EDI200. Pups of treated mothers, or treated pups were analyzed at weaning for the presence of sweat glands using an iodine/starch sweat test. Untreated WT and Tabby controls are shown for comparison. Timing of treatment is indicated on top of the pictures. The most relevant timings of treatment relative to tail hair induction are shown.
Figure 3B:
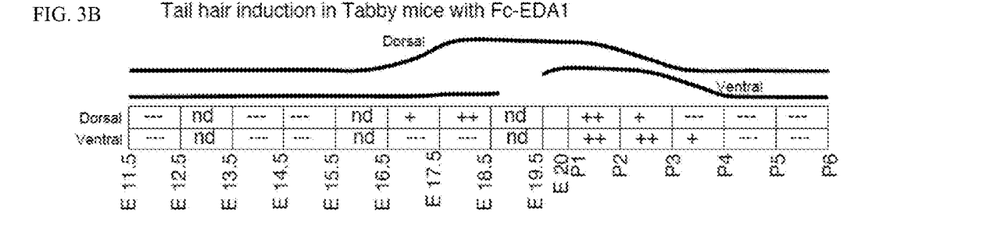
Figure 4A:
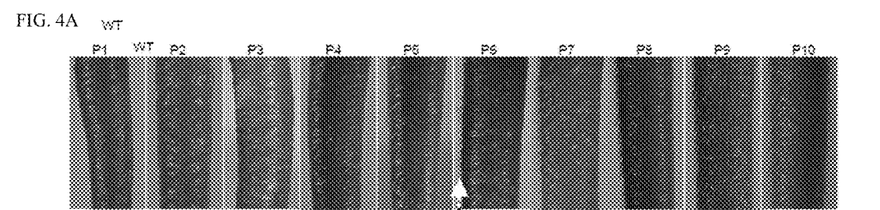
FIG. 4A: Pictures of the tail of a WT mouse were taken daily from birth (P1) to weaning (P21). The dorsal and ventral faces of the tail are on the left and right hand sides, respectively. Hair on the dorsal face of the tail is first apparent at P6 (arrow). Only the most relevant times are shown.
Figure 4B:
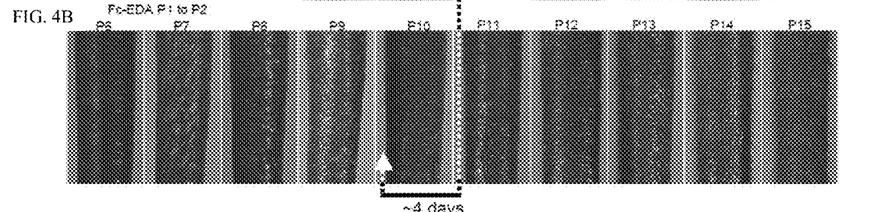
FIG. 4B: Pictures of the tail of an EDA-deficient Tabby mouse treated at P1 with EDI200 and 24 h later with an excess of EDAR-Fc were taken daily from birth (P1) to weaning (P21). Hair on the dorsal face of the tail is first apparent at P10 (arrow), i.e. about 4 days later than in a WT mouse. Only the most relevant times are shown.
Figure 4C:
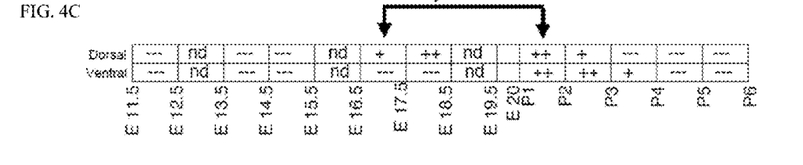
FIG. 4C: Same as FIG. 3B of FIG. 3, showing that approximately 4 days separate E16.5, which is the first time at which dorsal tail hair can be induced in Tabby mice, and P1, which is the initiation treatment time in the experiment shown in FIG. 4B. This, together with results shown in FIGS. 4A and 4B suggest that dorsal tail hair formation in Tabby mice treated at P1 with EDI200 stats with a delay of about 4 days compared to WT mice.
Figure 5A:
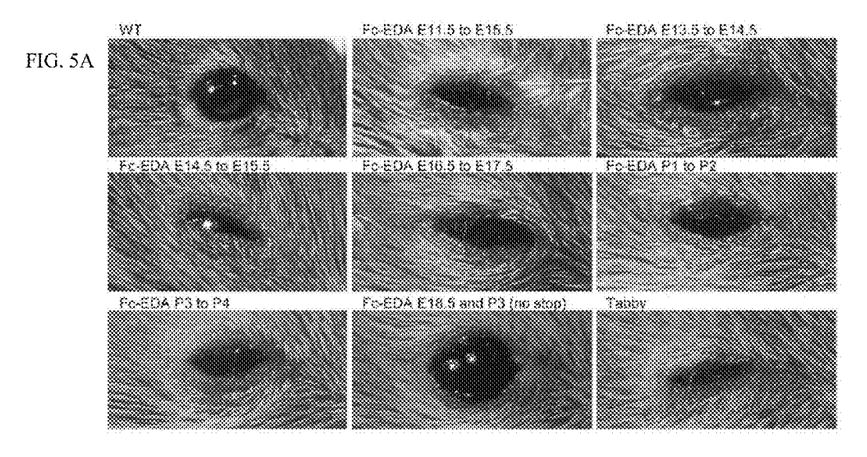
FIG. 5A: Pregnant EDA-deficient Tabby mice at days E11.5, E13.5, E14.5, E16.5, E17.5 of gestation or newborn Tabby pups at P1 (day of birth), P2, P3, P4 or P5 were administered EDI200 at 1 mg/kg iv (in mothers) or ip (in newborn), followed 24 h later by EDAR-Fc at 30 mg/kg to block remaining EDI200. In one instance, a pregnant mouse was administered EDI200 at 1 mg/kg at E18.5, and pups received again EDI200 at 1 mg/kg at P2, without any EDAR-Fc. Pups of treated mothers, or treated pups were analyzed at weaning for eye appearance. Untreated WT and Tabby controls are shown for comparison. Timing of treatment is indicated on top of the pictures. The most relevant timings of treatment relative to eye reversion are shown. Note that for mice treated at E18.5 and P3, only one out of three mice had a clearly reverted eye phenotype.
Figure 5B:
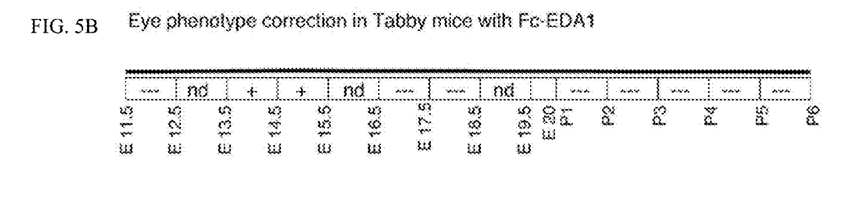
Figure 6A:
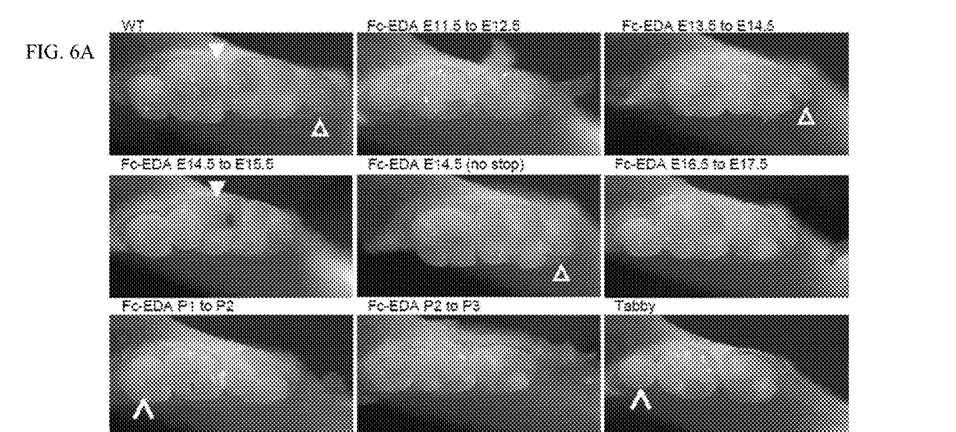
FIG. 6A: Pregnant EDA-deficient Tabby mice at days E11.5, E13.5, E14.5, E16.5, E17.5 of gestation or newborn Tabby pups at P1 (day of birth), P2, P3, P4 or P5 were administered EDI200 at 1 mg/kg iv (in mothers) or ip (in newborn), followed 24 h later by EDAR-Fc at 30 mg/kg to block remaining EDI200. In one instance, a pregnant Tabby mouse was treated at E14.5 with EDI200 but without injection of EDAR-Fc 24 h later (E14.5 (no stop)). Pups of treated mothers, or treated pups were sacrificed at about one month of age and analyzed for tooth morphology in the lower jaw. Untreated WT and Tabby controls are shown for comparison. Timing of treatment is indicated on top of the pictures. The most relevant timings of treatment relative to teeth induction are shown. Full white arrowhead: characteristic shape of second molar from WT. Open arrowhead: anterior portion of the first molar. Slim arrowhead: Third molar. It is noteworthy that in Tabby mice, the third molar (small molar on the left hand side of the pictures) can be either present or absent.
Figure 6B:
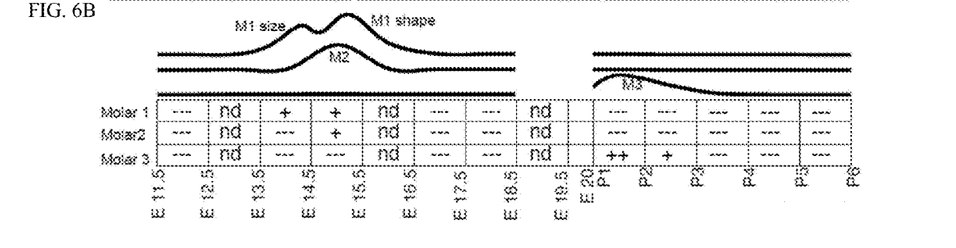

In this investigation concerning 24-hour exposure to 1 mg/kg EDI200 in the first 8 days prior to birth or in the 5 days following birth, it was found that the following phenotypes of the Tabby mice were corrected by EDI200 treatment in the time interval indicated. Representative photographs of the effects of EDI200 treatment compared to control animals are presented in FIGS. 1-6 and show the following:

a. No Tabby phenotypes were corrected in the offspring of pregnant Tabby mice administered both EDI200 and EDAR on Day E13.5 (data not shown).

b. Exposure to EDI200 of embryos at E14.5 without subsequent exposure to EDAR-Fc restored additional WT features (some sweat glands, some tail hair, hair behind ears, molar morphology) compared to the same treatment where EDAR-Fc was subsequently administered at E15.5 (FIG. 6 and data not shown).

c. Development of guard hairs (E13.5 to E15.5). Guard hair were rescued by EDI200 treatment at E14.5, not interrupted, and by 24 h exposure at E14.5 (3/3 mice). 24 h exposure at E13.5 rescued just few guard hairs (in 2/3 mice). No effect was seen at the earlier or late time points examined. See FIG. 1.

d. Development of sweat glands (E17.5 to P5). Few sweat glands were rescued by EDI200 treatment at E14.5, not interrupted, and numerous sweat glands were rescued by EDI200 treatment at P1, not interrupted. No sweat glands were rescued by 24 h exposure at E16.5 or earlier. Sweat glands were rescued by 24 h exposure to EDI200 at E17.5 (few sweat glands) or at P1 to P5 (numerous sweat gands). See FIG. 2.

e. Development of teeth (E13.5 to E16.5). The first molar was rescued by EDI200 treatment at E14.5, not interrupted. For the 24 h stimulus treatment groups, an effect was seen at E14, with partially enlarged molar (2/3 mice). The 2nd (lower) molar was rescued by treatment at E14.5 or E16.5 (3/3 mice at each time point). See FIG. 6.

f. Development of tail hair (E16.5 to P4). Tail hairs were rescued on the dorsal face by EDI200 treatment at E14.5, not interrupted and by EDI200 treatment at P1, not interrupted. Dorsal tail hair was also rescued by 24 h exposure at E16.5, E17.5, P1, or P2. Tail hairs were rescued on the ventral face by EDI200 treatment at E14.5, not interrupted, and by treatment at P1, not interrupted. Ventral tail hair was also rescued by 24 h exposure at P1, P2 or P3. No effect was observed at earlier or later time points. See FIG. 4.

g. Eye reversion in Tabby mice doesn't seem to be rescued at any 24 h period at the dose used in this experiment, nor by treatment at E14.5 or P1, not interrupted. However, eye reversion could be achieved upon longer EDI200 treatment (E18.5 and P3, no interruption with EDAR-Fc. But in this case only 1/3 pups had reverted eye appearance). See FIG. 5.

h. Development of hairs behind ear (E14.5 to E16.5). Hairs behind ears were rescued by EDI200 treatment at E14.5 and not interrupted. Some rescue by 24 h exposure at E14.5, and little rescue at E16.5 (data not shown).

i. No clear impact of EDI200 treatment on tail kink was established.

Example 3. Dosage Determination

In order to determine the minimal exposure time needed to obtain the full therapeutic activity of EDI200 to alter or correct phenotype, the methods of Swee et al. were performed (Swee L K, Ingold-Salamin K, Tardivel A, Willen L, Gaide O, Favre M, Demotz S, Mikkola M, Schneider P. (2009) J. Biol. Chem. 284: 27567-27576).

As in previous studies, it was found that injection of EDAR-Fc earlier than 3.5 hours following administration of 2 μg EDI200 prevented growth of hair on the tail, while EDAR-Fc was no longer effective when injected >3.5 hours after EDI200 treatment.

Considering that the elimination half-life of EDI200 (45 hours) is estimated to be at least 10 times longer than the exposure period needed to obtain a biological effect, the elimination half-life of EDI200 is not limiting its therapeutic activity, at least when induction of tail hair is considered.

What is claimed is:

1. A method for treating hypohidrotic ectodermal dysplasia in a mammalian organism diagnosed with or suspected of having hypohidrotic ectodermal dysplasia comprising administering a pharmaceutical composition comprising a hexamer of recombinant proteins, each of said proteins consisting of the amino acid sequence of SEQ ID NO: 1 and being glycosylated, to the organism by treatment of the mother of the organism, wherein the treatment of hypohidrotic ectodermal dysplasia is for correcting, altering or mitigating phenotypic presentations associated with hypohidrotic ectodermal dysplasia, and wherein said treatment of the mother is parenterally by a method selected from the group consisting of in utero injection, intravenous injection, or intra-arterial injection.

2. The method of claim 1, wherein the pharmaceutical composition is administered to the mother at a period during gestation selected from the group consisting of: after fertilization but before implantation, after implantation, between weeks 5-9 of gestation, between weeks 6-8 of gestation, during week 6 of gestation, during week 7 of gestation, during week 8 of gestation and after week 8 of gestation.

3. The method of claim 2, wherein the hypohidrotic ectodermal dysplasia is X-linked hypohidrotic ectodermal dysplasia (XLHED).

4. The method of claim 3, wherein the mammalian organism is a human.

5. The method of claim 3, wherein the phenotypic presentation is lack or abnormal morphology of various types of hair or alopecia and wherein the administration is between weeks 6-8 of gestation or during a delayed treatment window, wherein said delayed treatment window comprises 4 to 10 days.

6. The method of claim 3, wherein the phenotypic presentation is abnormal morphology or lack of sweat glands and wherein the administration is after week 8 of gestation or after birth.

7. The method of claim 3, wherein the phenotypic presentation is missing teeth or abnormally shaped teeth and administration is between weeks 5-9 of gestation.

\* \* \* \* \*

SEQUENCE LISTING

```
<160> NUMBER OF SEQ ID NOS: 1

<210> SEQ ID NO 1
<211> LENGTH: 380
<212> TYPE: PRT
<213> ORGANISM: artificial
<220> FEATURE:
<223> OTHER INFORMATION: Artificial Sequence (synthesized fusion
      polypeptide)

<400> SEQUENCE: 1

Lys Thr His Thr Cys Pro Pro Cys Pro Ala Pro Glu Leu Leu Gly Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Ser His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Asp Glu Leu Thr Lys Asn Gln Val Ser Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys Ala Asp Lys Ala Gly Thr Arg Glu Asn Gln Pro Ala Val Val
```

-continued

```
            225                 230                 235                 240

His Leu Gln Gly Gln Gly Ser Ala Ile Gln Val Lys Asn Asp Leu Ser
                245                 250                 255

Gly Gly Val Leu Asn Asp Trp Ser Arg Ile Thr Met Asn Pro Lys Val
                260                 265                 270

Phe Lys Leu His Pro Arg Ser Gly Glu Leu Glu Val Leu Val Asp Gly
                275                 280                 285

Thr Tyr Phe Ile Tyr Ser Gln Val Glu Val Tyr Tyr Ile Asn Phe Thr
            290                 295                 300

Asp Phe Ala Ser Tyr Glu Val Val Val Asp Glu Lys Pro Phe Leu Gln
305                 310                 315                 320

Cys Thr Arg Ser Ile Glu Thr Gly Lys Thr Asn Tyr Asn Thr Cys Tyr
                325                 330                 335

Thr Ala Gly Val Cys Leu Leu Lys Ala Arg Gln Lys Ile Ala Val Lys
                340                 345                 350

Met Val His Ala Asp Ile Ser Ile Asn Met Ser Lys His Thr Thr Phe
            355                 360                 365

Phe Gly Ala Ile Arg Leu Gly Glu Ala Pro Ala Ser
            370                 375                 380
```